United States Patent
Tanev et al.

(10) Patent No.: US 9,079,169 B2
(45) Date of Patent: Jul. 14, 2015

(54) METHANE AROMATIZATION CATALYST, METHOD OF MAKING AND METHOD OF USING THE CATALYST

(75) Inventors: Peter Tanev Tanev, Katy, TX (US); Armin Lange De Oliveira, Heidelberg (DE)

(73) Assignee: Shell Oil Company, Houston, TX (US)

( * ) Notice: Subject to any disclaimer, the term of this patent is extended or adjusted under 35 U.S.C. 154(b) by 557 days.

(21) Appl. No.: 13/105,499

(22) Filed: May 11, 2011

(65) Prior Publication Data

US 2012/0123176 A1     May 17, 2012

Related U.S. Application Data

(60) Provisional application No. 61/333,995, filed on May 12, 2010.

(51) Int. Cl.
| | |
|---|---|
| *B01J 37/02* | (2006.01) |
| *B01J 23/28* | (2006.01) |
| *B01J 29/076* | (2006.01) |
| *B01J 29/48* | (2006.01) |
| *B01J 37/08* | (2006.01) |
| *C07C 2/76* | (2006.01) |
| *B01J 35/02* | (2006.01) |

(52) U.S. Cl.
CPC .............. *B01J 37/0203* (2013.01); *B01J 23/28* (2013.01); *B01J 29/076* (2013.01); *B01J 29/48* (2013.01); *B01J 37/08* (2013.01); *B01J 37/086* (2013.01); *C07C 2/76* (2013.01); *B01J 35/023* (2013.01); *C07C 2521/04* (2013.01); *C07C 2521/06* (2013.01); *C07C 2521/08* (2013.01); *C07C 2523/06* (2013.01); *C07C 2523/08* (2013.01); *C07C 2523/10* (2013.01); *C07C 2523/14* (2013.01); *C07C 2523/20* (2013.01); *C07C 2523/22* (2013.01); *C07C 2523/26* (2013.01); *C07C 2523/28* (2013.01); *C07C 2523/30* (2013.01); *C07C 2523/34* (2013.01); *C07C 2523/36* (2013.01); *C07C 2523/42* (2013.01); *C07C 2523/46* (2013.01); *C07C 2523/50* (2013.01); *C07C 2523/72* (2013.01); *C07C 2523/745* (2013.01); *C07C 2523/75* (2013.01); *C07C 2523/755* (2013.01); *C07C 2529/40* (2013.01); *C07C 2529/65* (2013.01)

(58) Field of Classification Search
CPC ...... B01J 37/0203; B01J 37/086; B01J 37/08; B01J 29/076; B01J 29/48; B01J 23/28; B01J 35/023; B01J 23/14; B01J 29/40
USPC ...................... 502/76, 77, 300–355
See application file for complete search history.

(56) References Cited

U.S. PATENT DOCUMENTS

| | | | | |
|---|---|---|---|---|
| 2,889,287 A | | 6/1959 | Scott .............................. | 252/455 |
| 3,763,256 A | | 10/1973 | Massie .......................... | 260/668 |
| 3,912,660 A | * | 10/1975 | Tsigdinos et al. ............ | 502/321 |
| 3,997,431 A | | 12/1976 | Beuther et al. ................ | 208/216 |
| 4,374,045 A | * | 2/1983 | Chu ............................... | 502/77 |
| 4,940,827 A | | 7/1990 | Janssen et al. ................ | 585/646 |
| 5,227,557 A | * | 7/1993 | Bournonville et al. ........ | 585/419 |
| 7,550,637 B2 | | 6/2009 | Lowe et al. .................... | 585/261 |
| 7,589,246 B2 | | 9/2009 | Iaccino et al. ................ | 585/407 |
| 8,742,189 B2 | * | 6/2014 | Kiesslich et al. ............ | 585/417 |
| 2005/0143610 A1 | | 6/2005 | Mitchell et al. | |
| 2006/0035780 A1 | * | 2/2006 | Xu et al. ......................... | 502/66 |
| 2007/0134145 A1 | * | 6/2007 | Strehlau et al. ............ | 423/213.5 |
| 2007/0238605 A1 | * | 10/2007 | Strehlau et al. ................ | 502/60 |
| 2007/0249740 A1 | | 10/2007 | Iaccino et al. ................ | 518/726 |
| 2007/0249880 A1 | | 10/2007 | Iaccino et al. ................ | 585/418 |
| 2008/0051617 A1 | | 2/2008 | Sangar et al. ................ | 585/403 |
| 2008/0058564 A1 | | 3/2008 | Iaccino et al. ................ | 585/322 |
| 2008/0249342 A1 | | 10/2008 | Iaccino et al. ................ | 585/402 |
| 2009/0029852 A1 | | 1/2009 | Hagemeyer .................. | 502/312 |
| 2009/0030253 A1 | | 1/2009 | Xu et al. ........................ | 585/417 |
| 2009/0076316 A1 | * | 3/2009 | Ichikawa et al. ............ | 585/419 |
| 2009/0286678 A1 | | 11/2009 | Hagemeyer .................. | 502/304 |

FOREIGN PATENT DOCUMENTS

| | | | |
|---|---|---|---|
| EP | 1980319 | 10/2008 | |
| GB | 901588 | 7/1962 | |
| JP | 201042348 | 2/2010 | |
| WO | WO2006068814 | 6/2006 | |
| WO | WO2007067285 | 6/2007 | ............... C07C 2/76 |
| WO | WO2007123523 | 11/2007 | ............... C07C 2/76 |
| WO | WO2009020045 | 2/2009 | ............... C07C 2/76 |
| WO | WO2009076005 | 6/2009 | ............... C07C 2/76 |
| WO | WO2009091336 | 7/2009 | ............... B01J 29/06 |
| WO | WO2009106474 | 9/2009 | ............... B01J 23/00 |
| WO | WO 2009124960 A1 * | 10/2009 | |
| WO | 2009140790 | 11/2009 | |

OTHER PUBLICATIONS

Wang, L, et al: Dehydrogenation and Aromatization of Methane under Non-Oxidizing Conditions, Catalysis Letters21 (1993), pp. 35-41.

Dong, Qun, et al., "Studies on Mo HZSM-5 Complex Catalyst for Methane Aromatization", Journal of Natural Gas Chemistry, 2004, pp. 36-40.

PCT International Searching Authority report dated Feb. 17, 2012, Application No. PCT/US2011/036053 filed May 11, 2011.

* cited by examiner

*Primary Examiner* — Anthony J Zimmer

(57) ABSTRACT

A catalyst for converting methane to aromatic hydrocarbons is described herein. The catalyst comprises an active metal or a compound thereof, and an inorganic oxide support wherein the active metal is added to the support in the form of metal oxalate. The metal oxalate-derived catalyst exhibits superior performance in the conversion of methane-rich feed to aromatics products relative to catalysts prepared from non-oxalate metal precursors. A method of making the catalyst and a method of using the catalyst are also described.

13 Claims, 4 Drawing Sheets

METHANE AROMATIZATION CATALYST, METHOD OF MAKING AND METHOD OF USING THE CATALYST

This application claims priority to U.S. Provisional Application No. 61/333,995, filed on May 12, 2010, which is herein incorporated by reference.

FIELD

This invention relates to a catalyst useful in converting methane to aromatic hydrocarbons, a method of making the catalyst and a method of using the catalyst to convert methane to aromatic hydrocarbons.

BACKGROUND

The aromatic hydrocarbons (specifically benzene, toluene and xylenes), are the main high-octane bearing components of the gasoline pool and important petrochemicals used as building blocks to produce high value chemicals and a variety of consumer products, for example, styrene, phenol, polymers, plastics, medicines, and others. Aromatics are primarily produced from oil-derived refinery feedstocks in such processes as catalytic reforming and cracking of heavy naphthas. However, the recent severe oil shortages and price spikes resulted in severe aromatics shortages and price spikes. Therefore, there is a need to develop new commercial routes to produce high value aromatics from highly abundant and cheap hydrocarbon feedstocks, for example, methane or stranded natural gas (typically containing about 80-90% methane).

There are enormous proven stranded natural gas reserves around the world. According to some estimates, the natural gas reserves are at least equal to those of oil. However, unlike the oil reserves which are primarily concentrated in a few oil-rich countries and are properly and extensively exploited, upgraded and monetized, the natural gas reserves are much more broadly distributed around the world and significantly underutilized. Many developing countries that have significant natural gas reserves lack the proper infrastructure to exploit them and convert them to higher value products. Quite often, in such situations, natural gas is flared to the atmosphere and wasted. Because of the above reasons, there is enormous economic incentive to develop new technologies that can efficiently convert methane or natural gas to higher value chemical products, specifically aromatics.

In 1993, Wang et al., (*Catal. Lett.* 1993, 21, 35-41), discovered that methane can be partially converted to benzene at atmospheric pressure and a temperature of 700° C. over a catalyst containing 2.0 wt % molybdenum deposited on H-ZSM-5 zeolite support. Significantly, low methane conversion of less than 10% but very high benzene selectivity of 100% were observed in these experiments. Subsequently, other researchers repeated the above work and found that Wang et al. did not quite identify all of the reaction products (naphthalene and others) and that when all of the products are identified the benzene selectivity falls in the range of 60-70%. These other researchers also pointed out that, the catalyst cokes up and deactivates very rapidly—as manifested by complete loss of activity after about 4-5 hrs on stream. Since Wang's discovery, many academic and industrial research groups have contributed to further developing various aspects of the methane to benzene catalyst and process technology. Many catalyst formulations have been prepared and tested and various reactor and process conditions and schemes have been explored.

Despite these efforts, there is still no commercial methane aromatization or methane to benzene catalyst and process. The vast majority of researchers agree that the main obstacles to developing and commercializing an efficient, direct methane to benzene process are the low methane conversion (still remaining at around 7-10%) and rapid coke formation and catalyst deactivation.

Therefore, there is a need to develop new methane aromatization catalysts that provide higher methane conversion at equal or higher selectivity to benzene relative to the prior art. Also, there is a need to develop catalysts that exhibit lower coking and deactivation rates, i.e. better sustain their methane conversion and benzene selectivity performance over the course of time (exhibit better stability) relative to the catalysts of the prior art.

SUMMARY OF THE INVENTION

The invention provides a methane aromatization catalyst comprising an active metal or a compound thereof, and an inorganic oxide support wherein the active metal is added to the support as a metal oxalate. Preferably, the catalyst comprises molybdenum as the active metal and a zeolite as the inorganic support.

The invention further provides a process for preparing a methane aromatization catalyst comprising: contacting an active metal oxalate with an inorganic oxide support to form a mixture, and calcining the mixture.

The invention still further provides a process for producing aromatic hydrocarbons comprising contacting a gas stream comprising methane with a catalyst comprising molybdenum where the catalyst was prepared by contacting a molybdenum oxalate with a zeolite-containing support.

DETAILED DESCRIPTION

The methane aromatization catalyst described here comprises an active metal and an inorganic oxide support. The active metal may be any metal that exhibits catalytic activity when contacted with a stream comprising methane under methane aromatization conditions. The active metal may be selected from the group consisting of: vanadium, chromium, manganese, iron, cobalt, nickel, copper, zinc, gallium, germanium, niobium, molybdenum, ruthenium, rhodium, silver, tantalum, tungsten, rhenium, platinum and lead and mixtures thereof. The active metal is preferably molybdenum.

The inorganic oxide support can be any support that, when combined with the active metal contributes to the overall catalyst performance exhibited in the methane aromatization reaction. The support has to be suitable for treating or impregnating with the active metal or compound thereof. The inorganic support preferably has a well developed porous structure with sufficiently high surface area and pore volume and suitable surface acidity. The inorganic oxide support may be selected from the group consisting of: zeolites, non-zeolitic molecular sieves, silica, alumina, zirconia, titania, yttria, ceria, rare earth metal oxides and mixtures thereof. The inorganic oxide support contains zeolite as the primary component. The zeolite may be of a ZSM-5, ZSM-22, ZSM-8, ZSM-11, ZSM-12 or ZSM-35 zeolite structure type. Preferably, the support of this invention comprises ZSM-5 zeolite. The ZSM-5 zeolite further may have a $SiO_2/Al_2O_3$ ratio of 10 to 100. Preferably, the $SiO_2/Al_2O_3$ ratio of the ZSM-5 zeolite of this invention is in the range of 20-50. Even more preferably, the $SiO_2/Al_2O_3$ ratio is from 20 to 40 and most preferably about 30. The zeolite support could further contain about 10-30% wt of inorganic oxide binder that allows for shaping of the catalyst in the desired form and for achieving the high mechanical strength and abrasion resistance desired for commercial operation. The binder may be selected from the group of silica, alumina, zirconia, titania, yttria, ceria, rare earth oxides or mixtures thereof.

The active metal or compound thereof is added to the support from a metal oxalate precursor. If the metal oxalate is not commercially available, the active metal or compound thereof is reacted with oxalic acid to form the desired metal oxalate precursor. The metal oxalate precursor can be formed by adding the necessary amount of metal oxide powder to a solution of oxalic acid. Preferably, the metal oxide powder is $Mo(VI)O_3$. The mixture may be stirred and/or heated as necessary to obtain a clear solution of the metal oxalate.

The inorganic oxide support can be mixed with the metal oxalate to afford a solid state mixture that can then be subjected to calcination in an oven under dry air flow atmosphere to evaporate and deposit the active metal in the pores of the zeolite. This technique is known to those skilled in the art as solid state ion-exchange. In a more preferred embodiment, the inorganic support is impregnated with metal oxalate by adding a metal oxalate precursor solution to a vessel containing the necessary amount of inorganic oxide support. The support is left in contact with the solution for a sufficient time to allow the metal oxalate to penetrate the pores of the support and react with the active centers of the zeolite.

Other components or promoters can be added to the support in various precursor forms and impregnation order to improve various aspects of the finished catalyst physical or mechanical properties or catalytic performance. For example, a promoter precursor could be added to the support in a mixing or impregnation step before, after or simultaneously with the active metal oxalate.

The support, now impregnated with metal oxalate, is dried and calcined to form the finished methane aromatization catalyst of this invention. The drying and calcination steps typically include flowing dry air or nitrogen in a volume of from 1 to 60 liters per hour over the catalyst precursor, preferably from 20 to 50 liters per hour. The impregnated support may be subjected to a series of specific heating rates and temperature ramps to complete the cross-linking of the structure and to form the finished active metal oxide/zeolite comprising methane aromatization catalyst of the invention.

The impregnated support is preferably dried and calcined by heating it at a temperature of from 80° C. to 120° C. for a period of time of at least 20 minutes, preferably of from 60 minutes to 180 minutes. The temperature is then increased to from 275° C. to 325° C. at a rate of from 1° C. to 10° C. per minute, preferably from 2 to 4° C. per minute. That temperature is then maintained for a period of time of at least 20 minutes, preferably from 60 minutes to 180 minutes. Then, the temperature is again increased, this time to from 475° C. to 525° C. at a rate of 1° C. to 10° C. per minute, preferably from 2 to 4° C. per minute. This temperature is then maintained for at least 20 minutes, preferably from 20 minutes to 240 minutes, and even more preferably of from 120 minutes to 240 minutes.

The catalyst formed by the above steps is then preferably cooled to a temperature in the range of from 80° C. to 120° C.

The methane aromatization catalyst is useful in the reaction of methane or methane-rich gases, for example, natural gas, to form aromatic hydrocarbons. Natural gas is defined as a mixture of saturated hydrocarbons having a carbon number of from 1 to 5, preferably of from 1 to 4.

The conversion of methane-containing gas to aromatic hydrocarbons is typically carried out in a reactor comprising a catalyst which is active in the conversion of methane to aromatics. The methane containing gas that is fed to the reactor contains more than 50% vol. methane, preferably more than 75% vol. methane and even more preferably of from 75% vol. to 100% vol. methane.

The conversion of methane-containing gas is carried out at a space velocity of from 100 to 10000 $h^{-1}$, a pressure of from 0.5 to 10 bar and a temperature or from 500 to 850° C. More preferably, the conversion is carried out at space velocity of from 300 to 3000 $h^{-1}$, a pressure of from 0.5 to 5 bar and a temperature of from 600 to 800° C. Even more preferably, the conversion is carried out at space velocity of from 500 to 1500 $h^{-1}$, a pressure of from 0.5 to 1 bar and a temperature of from 650 to 750° C. Various co-feeds such as CO, $CO_2$ or $H_2$ that react with the coke precursors or subdue or prevent their formation during the methane aromatization reaction could be added at levels of <10% vol. to the methane-containing feed to improve the stability performance or regenerability of the catalyst. The methane aromatization reaction is then carried out until methane conversion falls to values that are lower than those that are economically acceptable. At this point, the catalyst is regenerated to restore its methane aromatization activity. Following the regeneration, the catalyst is again contacted with a methane-containing feed in a subsequent process cycle.

The catalyst regeneration can be performed by different techniques known to those skilled in the art that are effective in removing the carbonaceous deposits and restoring the catalyst activity. For this particular invention, the spent catalysts were regenerated by first cooling them from methane aromatization reaction temperature to 480° C. and then subjecting them to purging with argon at 1000 $h^{-1}$, atmospheric pressure and 480° C. for one hour. Next, the catalysts were subjected to 2000 $h^{-1}$ of 0.5 to 2.0% vol. $O_2/N_2$ gas flow at atmospheric pressure and 480° C. for 22 hrs to slowly burn off the coke from their surface and restore their methane aromatization activity.

EXAMPLES

The following Examples were carried out to compare the catalytic performance of the methane aromatization catalyst of this invention, prepared from molybdenum oxalate, with the catalysts described in the prior art prepared from other (non-oxalate containing) molybdenum precursors. The molybdenum precursor and concentration level as well as the catalyst preparation method were varied in these examples.

To remove any performance differences caused by the inorganic oxide support, all catalysts described in the examples were prepared using the same H-ZSM-5 zeolite support. The support was prepared by calcining a batch of commercially available Zeolyst International Company, CBV-3024E, $NH_4^+$/ZSM-5 zeolite powder with $SiO_2/Al_2O_3$ ratio of 30 under dry air at 500° C. for a sufficient period of time to convert it from $NH_4^+$ into $H^-$ form.

The performance tests of all catalysts were conducted in the same manner. Prior to testing, the catalysts were loaded into the reactors as 2.5 cc charges and pretreated in situ by: (i) establishing a 5 L/hr flow of pure $H_2$, at 1 bar pressure and heating from ambient temperature to 240° C. at 0.5° C./min and holding at 240° C. for 4 hrs; (ii) heating under the same flow and pressure to 480° C. at 2° C./min and holding at 480° C. for 2 hrs and (iii) finally, heating under the same conditions to 700° C. at 2° C./min and holding at 700° C. for at least 1.5 hours to complete the reduction. The catalysts were purged with 2.5 L/hr of pure argon for 20 min and then contacted with a methane-containing feed comprising 90% vol. methane and 10% vol. argon at 1000 $hr^{-1}$ GHSV, 1 bar pressure and 700° C. The argon was used as an internal standard for the GC analysis.

Figure 1:
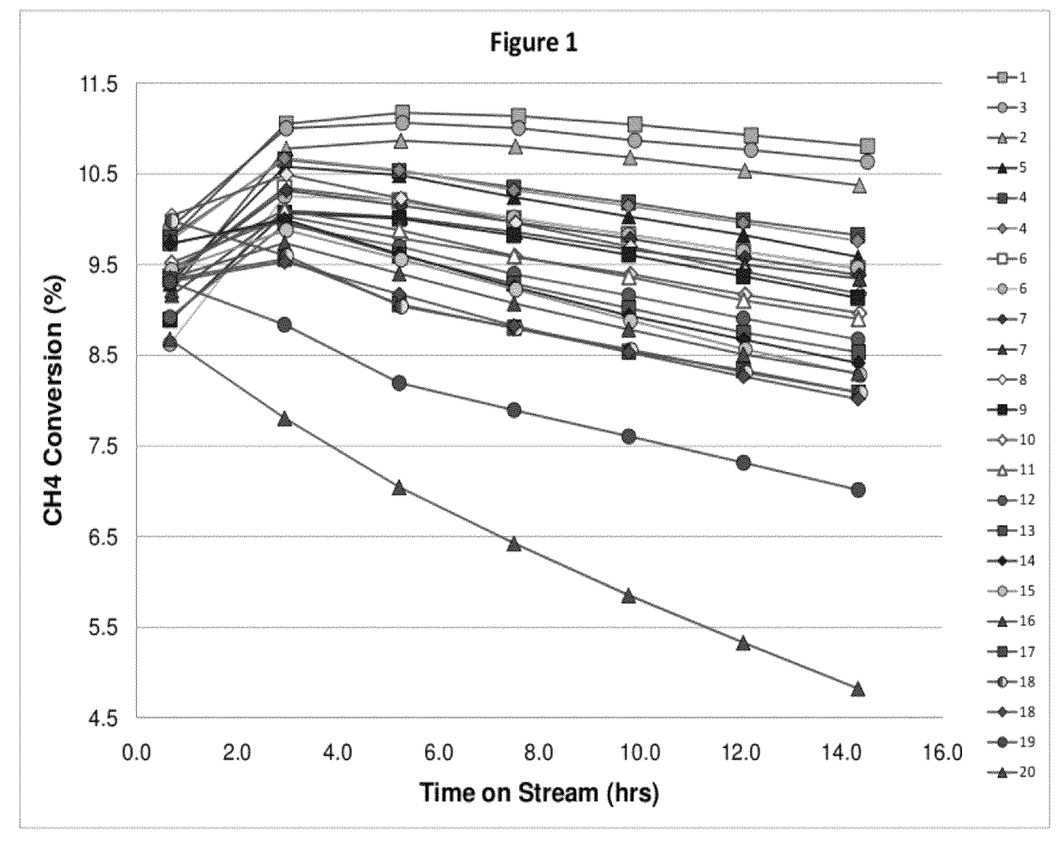
FIG. 1 shows the methane ($CH_4$) conversion versus time on stream data obtained for the catalysts described in the Examples.

During the tests, full product samples were automatically withdrawn from the reactor zone located directly under the catalyst bed every 20 minutes and analyzed with a GC analyzer. The methane conversion versus time on stream performance data obtained for all catalysts (see Examples 1-20) is shown in FIG. 1. The figure shows that the catalysts prepared from molybdenum oxalate precursor (Examples 1-3), provide higher methane conversion than catalysts prepared with other (non-oxalate) molybdenum precursors (Examples 4-20). The figure also shows that the molybdenum oxalate-derived catalysts maintain their methane conversion better (exhibit better stability) than the catalysts derived from non-oxalate precursors.

Figure 2:
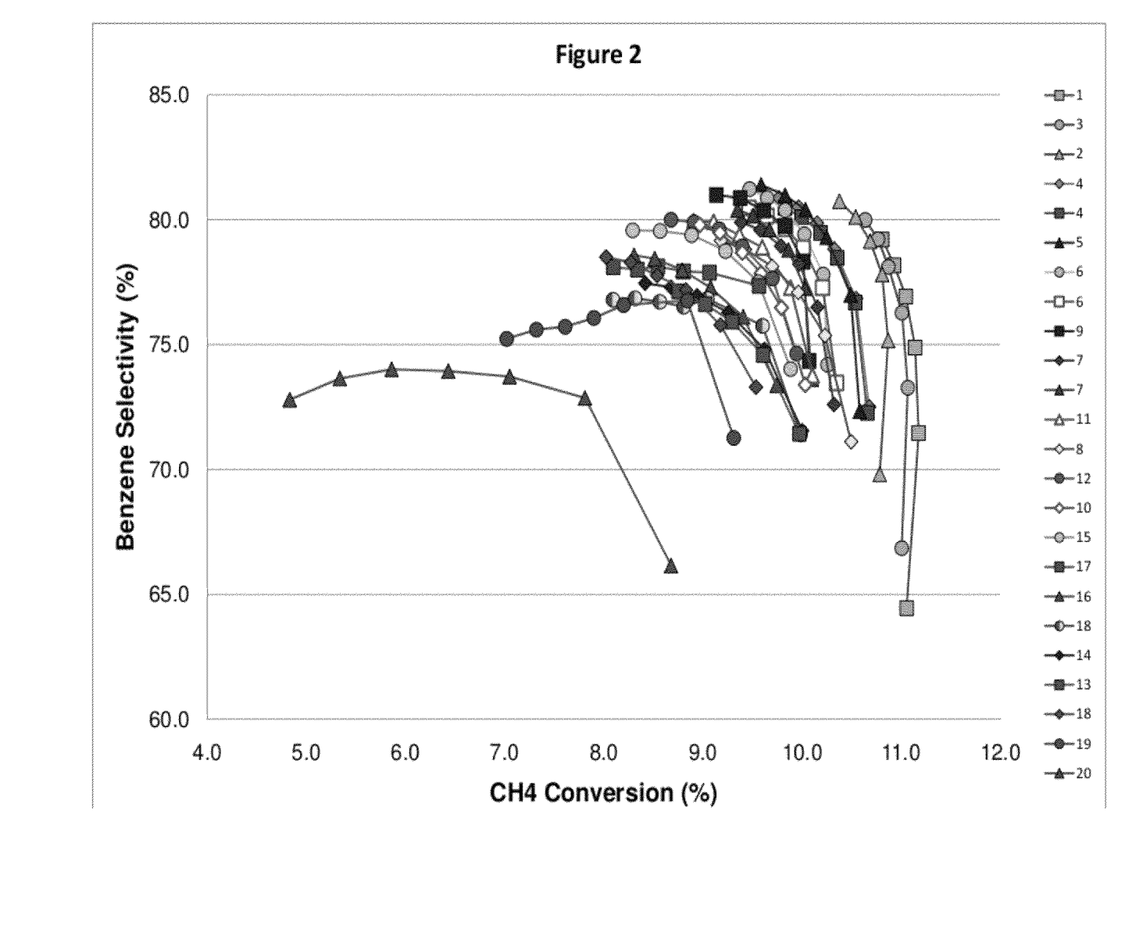
FIG. 2 shows the benzene selectivity versus methane ($CH_4$) conversion data obtained for the catalysts described in the Examples.

FIG. 2 shows the corresponding benzene selectivity versus methane conversion obtained in these tests. The data show, that the catalysts prepared from a molybdenum oxalate precursor (Examples 1-3), provide higher benzene selectivity at higher methane conversion than the catalysts prepared from non-oxalate precursors (Examples 4-20). It should also be noted that, at the same molybdenum loading level, the molybdenum oxalate-derived catalysts exhibit higher methane conversion and higher benzene selectivity and better stability relative to catalysts prepared using non-oxalate precursors. This performance benefit was observed for catalysts with very broad 4-15% wt of molybdenum loading. In addition, among these catalysts, the 6-10% wt molybdenum containing catalysts prepared from molybdenum oxalate precursors exhibited the best combination of higher methane conversion, benzene selectivity and performance stability relative to all other catalysts.

Following the above tests, the spent catalysts were subjected to regeneration. The regeneration was carried out in situ by first cooling the catalysts to 480° C. and then purging them with argon at 1000 $h^{-1}$, 1 bar and 480° C. for 1 hr. Next, the catalysts were subjected to 2000 $h^{-1}$ of 0.5 to 2.0% vol. $O_2/N_2$ gas flow at atmospheric pressure and 480° C. for 22 hrs to slowly burn off the coke from the surface of the catalysts and restore their activity. The regenerated catalysts were then subjected to performance testing.

Figure 3:
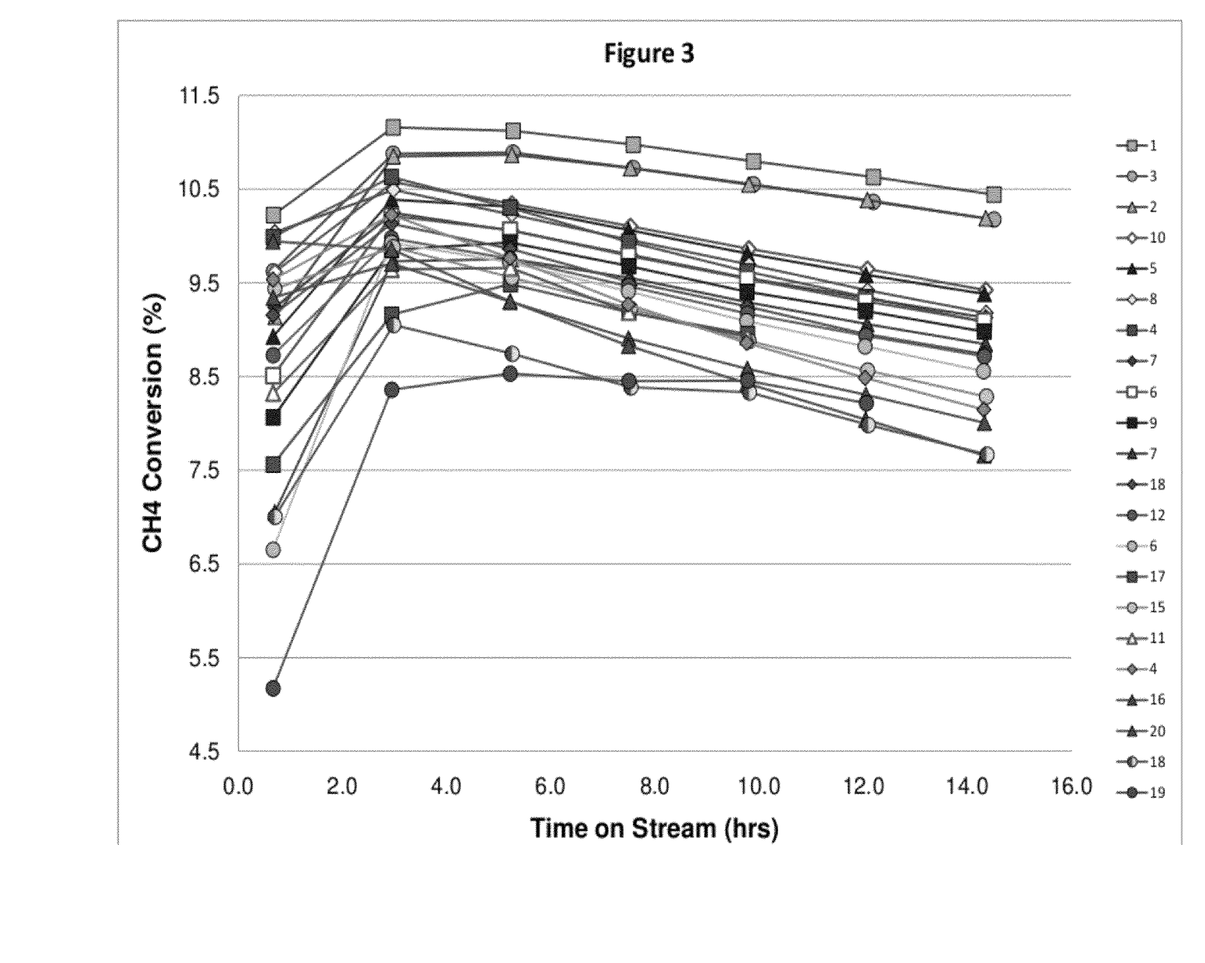
FIG. 3 shows the methane ($CH_4$) conversion versus time on stream data obtained for the catalysts described in the Examples after they have been spent and regenerated.
Figure 4:
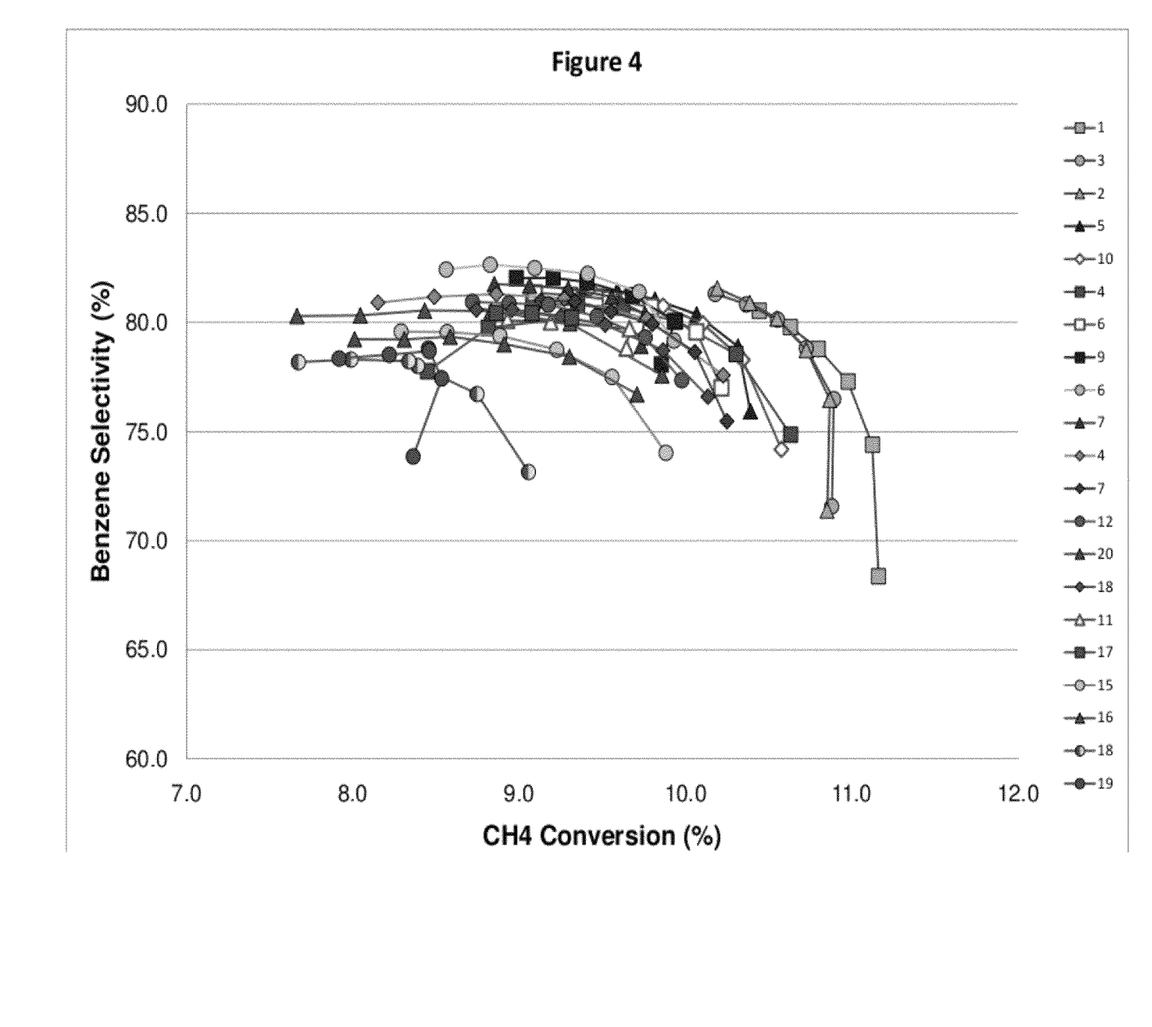
FIG. 4 shows the benzene selectivity versus methane ($CH_4$) conversion data obtained for the catalysts described in the Examples after they have been spent and regenerated.

FIGS. 3 and 4 show the methane conversion versus time on stream and benzene selectivity versus methane conversion test data, respectively, for the regenerated catalysts. Again, the data show that the regenerated catalysts prepared from molybdenum oxalate precursors exhibit higher methane conversion and benzene selectivity and higher stability relative to the regenerated catalysts which were prepared from other molybdenum presursors.

The aforementioned catalysts were prepared as described in the following Examples.

Example 1

A molybdenum oxalate solution was prepared by dissolving 144.07 g of $MoO_3$ and 144.07 g of oxalic acid dihydrate (to give a molar ratio of molybdenum to oxalic acid of 1:1.14) in a 1000 mL beaker filled with deionized water in such a way as to prepare a total of 500 mL of 2 mol/L molybdenum oxalate solution. The solution is then heated to 80° C. and stirred for 4 hrs or until complete dissolution of the molybdenum oxide and formation of molybdenum oxalate.

Simultaneously, a sufficient quantity of $NH4^+$-ZSM-5 zeolite powder was shaped by compacting it in a compactor at 250 bar and then sieved to obtain a support particles fraction of from about 315-500 microns. The shaped $NH4^+$ form zeolite support particles were then placed in an oven and calcined at a temperature of 500° C. for 4 hours to convert them to an $H^+$ form.

Eight grams of the $H^+$-ZSM-5 zeolite support particles were then impregnated with the molybdenum oxalate solution as follows. The impregnation was carried out in a Perkin Elmer MultiProbe II ex robotic pipetor that allows for automated simultaneous impregnation of several support samples. First, the impregnated support was weighed into a shallow bed dish and spread evenly to maximize impregnation surface. The dish was then placed in the Perkin Elmer Multiprobe in preparation for impregnation. Next, a 2.66 mL quantity of the above described molybdenum oxalate impregnation solution was mixed with 2.94 g of deionized water and loaded in the pipetor. Then, the impregnation program was started and the robotic head gradually impregnated the support in the dish in reproducible manner.

The impregnated sample was then aged for 30 minutes; air dried and then calcined in a programmable oven by subjecting it to a 10 L/min flow of dry air and heating it to 300° C. at a rate of 1° C. per minute. The temperature was maintained for 18 hours. Then, the temperature was raised to 550° C. at a rate of 1° C. per minute and held for 2 hours. The calcined catalyst sample was then sieved to remove fines and to obtain the desired 315-500 microns fraction. The catalyst had a molybdenum content of 6.0% wt.

Example 2

The catalyst of this example was prepared in the same manner as the one in Example 1 except that 4.54 g (instead of 2.95 g) of deionized water were added to the 2.66 mL solution of molybdenum oxalate. In addition, the first step of the calcination of the impregnated catalyst at 300° C. was carried out for 2 hrs instead of 18 hrs. The finished catalyst contained 6.0% wt of molybdenum.

Example 3

The catalyst of this Example was prepared in the same manner as the catalyst of Example 1. The only difference in this preparation was the molybdenum loading. Specifically, 3.63 mL of the molybdenum oxalate solution and 1.97 mL of deionized water we used to prepare the impregnation solution and to achieve 8.0% w molybdenum loading. The finished catalyst had a molybdenum content of 8.0% wt.

Comparative Examples 4-20

Example 4

An ammoniumheptamolybdate solution was prepared by dissolving 3.247 g of ammoniumheptamolybdate in 10 mL of deionized water.

The zeolite support was prepared for impregnation following the same steps as described Example 1. Ten grams of the zeolite support, were impregnated with the aid of a pipette with 10 mL of the ammoniumheptamolybdate solution. The impregnation was carried out in a porcelain dish. Following the impregnation, the wet zeolite support was manually mixed with a spatula, aged for 0.5 hrs under shaking and then transferred to an oven for drying and calcination. The drying was carried out by heating under air flow of 1 L/min at a rate of 1° C. per minute to 120° C. and holding at 120° C. 10 hours. Then, the temperature was raised to 500° C. at a rate of 1° C. per minute and held for 6 hours. The finished catalyst sample was sieved to remove fines and to obtain the desired 315-500 microns fraction. The finished catalyst had a molybdenum content of 15.0% wt. It should be noted that this sample was tested twice.

Example 5

The catalyst of this example was prepared in the same manner as described in Example 4 except that the impregnating solution was prepared by mixing 4.63 g of ammoniumheptamolybdate with 25 mL of deionized water. Then, 5.07 mL of the above impregnation solution was mixed with 2.13 g of deionized water and this final solution was used to impregnate 8 g of zeolite support. Finally, a somewhat different drying and calcining procedure was employed as described below. The impregnated support was placed in a programmable oven and dried and calcined in a 1 L/min flow of dry air by ramping the temperature at a rate of 1° C./min to 300° C. and holding for 2 hrs and then ramping the temperature at the same rate to 550° C. and holding for 2 hrs. The finished catalyst sample was sieved to remove fines and to obtain the desired 315-500 microns fraction and then tested as described above. The catalyst was found to have a molybdenum content of 6.0% wt.

Example 6

The catalyst of this example was prepared in a similar manner as described in Example 5. In this case, an ammoniumheptamolybdate solution was prepared by dissolving 4.63 g of ammoniumheptamolybdate in 20 mL of water and adjusting the volume to 25 mL to provide a solution with a molybdenum concentration of 0.15 mol/L. Then, 11.03 mL of the above impregnating solution was used to impregnate 10 g of the zeolite support. The impregnated support was then placed in an oven and dried with air (1 L/min) by heating to 70° C. at a rate of 1° C. per minute and holding for 10 hours. Then, the temperature was increased to 120° C. at a rate of 1° C. per minute and held for another 10 hours. Finally, the temperature was increased to 500° C. at a rate of 1° C. per minute and held for 5 hours. The finished catalyst sample was sieved to remove fines and to obtain the desired 315-500 microns fraction and then tested as described above. The catalyst was found to have a molybdenum content of 10.0% wt.

It should be noted that this particular catalyst was tested twice.

Example 7

This example describes a methane aromatization catalyst prepared by physical mixing or the so-called "solid state ion-exchange" method. The zeolite support was prepared following the same steps as described in the preceding examples. Then, 6.383 g of $MoO_3$ powder were mixed with 100 g of the zeolite support. The mixing was carried out by first dividing the 106.4 g mix into ten separate 10.64 g portions. Next, the portions were mixed in a grinder one portion at a time. The physical mixture was then compacted in a Powtec compactor at a pressure force of 250 bar with 3 repetitions. The catalyst precursor was placed in a Microwave furnace CEM and heated with nitrogen (1 L/min) at a temperature of 25° C. for 4 hours. Then, the temperature was increased to 500° C. at a rate of 25° C. per minute and held for 2 more hours. The finished catalyst was sieved to remove fines and to obtain the desired 315-500 microns fraction. The catalyst was found to have a molybdenum content of 4.081% wt (equivalent to 6% wt of $MoO_3$).

Example 8

An impregnation solution was prepared by adding 28.08 g $MoO_3$ to 200 mL of deionized water and dissolving the oxide via careful addition of $NH_4OH$ (25 wt %) until the pH of the solution reached 9. The volume of the solution was then adjusted to a total of 250 mL by addition of more deionized water. The zeolite support was prepared for impregnation as described in the previous examples. A final impregnation solution was prepared by mixing 9.0 mL of the above molybdenum solution (having pH=9) with 0.5 mL of deionized water. The solution was then used to impregnate 10.5 g of the zeolite support particles in the Perkin Elmer Multiprobe II ex apparatus. The impregnation was accomplished as described in Example 1. The impregnated zeolite support was then placed in a programmable oven and dried and calcined under flow of dry air (1 L/min) by first increasing the temperature to 300° C. at a rate of 1° C. per minute and holding for 1 hour. Next, the temperature was increased to 550° C. at a rate of 1° C. per minute and held for 2 hours. The finished catalyst was sieved to remove fines and to obtain the desired 315-500 microns fraction. The catalyst was found to have a molybdenum content of 6.0% wt.

Example 9

The catalyst of this example was prepared as described in Example 7 except that 8.695 g $MoO_3$ (8.0% wt.) were mixed with 100 g of the zeolite support. The support was calcined using a conventional programmable oven rather than a microwave oven. Specifically, the impregnated support was dried by placing it in the oven and heating it at a rate of 1° C./min in dry air (1 L/min) to 300° C. and holding for 2 hours. Then the temperature was increased to 550° C. at a rate of 1° C. per minute and held for 2 hours. The finished catalyst was sieved to remove fines and to obtain the desired 315-500 microns fraction. The catalyst had a molybdenum content of 5.478% wt (equivalent to 8 wt % $MoO_3$).

Example 10

The catalyst of this Example was prepared in a similar manner as described in Example 6. An ammoniumheptamolybdate solution was prepared by dissolving 4.63 g of ammoniumheptamolybdate in 20 mL of deionized water and adjusting the volume to 25 mL to provide a solution with a molybdenum concentration of 0.15 mol/L. The zeolite was subjected to impregnation as a powder without shaping. The zeolite, 10 g, was impregnated with a solution comprising 6.4 mL of the ammoniumheptamolybdate solution and 2.7 mL of deionized water. The zeolite powder and the solution were manually mixed with a spatula. The impregnated support was dried and calcined by placing it in an oven and heating it with dry air (1 L/min) at a rate of 1° C./min to 70° C. and holding for 10 hours. Then the temperature was increased to 120° C. at a rate of 1° C. per minute and held for 10 hours. Finally, the temperature was increased to 500° C. at a rate of 1° C. per minute and held for 5 hours. The finished catalyst was sieved to remove fines and to obtain the desired 315-500 microns fraction. The catalyst had a molybdenum content of 6.0% wt.

Example 11

The catalyst of this example was prepared as described in Example 5 except that the impregnation solution was prepared by dissolving 3.09 g of ammoniumheptamolybdate in 25 mL of deionized water. Also, 10 g of the zeolite support was impregnated with 9.5 mL of the above impregnating solution without further dilution. The finished catalyst was sieved to remove fines and to obtain the desired 315-500 microns fraction. The catalyst had a molybdenum content of 6.0% wt.

Example 12

The catalyst was prepared as described in Example 5 but the drying and calcination procedure followed was the one described in Example 6. The finished catalyst was sieved to remove fines and to obtain the desired 315-500 microns fraction. The catalyst had a molybdenum content of 6.0% wt.

Example 13

An impregnating solution of molybdenum acetylacetonate was prepared by adding 13.89 g of molybdenum acetylacetonate to 57.6 mL of $HNO_3$ (30% wt). The zeolite support was prepared for impregnation as described in Example 1. The entire amount of impregnating solution was then used to impregnate 64 g of the zeolite support in a dish and then the impregnate was manually mixed with a spatula as described in Example 4. The impregnated zeolite was then dried and calcined under dry air flow of 1 L/min by increasing the temperature at a rate of 1° C./min to 300° C. and holding for 2 hours. Then the temperature was increased to 500° C. at a rate of 1° C. per minute and held for 2 hours. The finished catalyst was sieved to remove fines and to obtain the desired 315-500 microns fraction. The catalyst had a molybdenum content of 6% wt.

Example 14

The catalyst of this Example was prepared in the same way as described in Example 13 except that the final calcination temperature was 550° C. instead of 500° C.

Example 15

The zeolite was used as a powder without shaping. The zeolite was calcined at 500° C. for 4 hours to convert it to $H^+$ form. Next, 5.746 g $MoO_3$ (in solid form) was mixed with 60 g of the zeolite powder in a mortar grinder. The molybdenum oxide/zeolite mixture was then placed in a programmable oven and calcined under dry air flow of 1 L/min by increasing the temperature to 300° C. at a rate of 1° C. per minute. The temperature was maintained for 2 hours. Then, the temperature was increased to 550° C. at a rate of 1° C. per minute and held for 2 hours. The finished catalyst sample was sieved to remove fines and to obtain the desired 315-500 microns fraction. The catalyst had a molybdenum content of 4.081% wt (equivalent to 6% wt of $MoO_3$).

Example 16

The catalyst of this Example was prepared in a similar manner as the one of Example 5.

An ammoniumheptamolybdate solution was prepared by dissolving 4.63 g of ammoniumheptamolybdate in 20 mL of deionized water and adjusting the volume to 25 mL to provide a solution having a molybdenum concentration of 0.15 mol/L.

The zeolite support was shaped and calcined as described in Example 5. Then, 6.64 mL of the ammoniumheptamolybdate solution was mixed with 2.66 g of deionized water to form the final impregnation solution. The solution was used to impregnate 10 g of the zeolite support. The freshly impregnated zeolite was manually mixed with a spatula and aged for 0.5 hrs. The impregnated zeolite was then dried and calcined using exactly the same procedure as described in Example 6. The finished catalyst was sieved to remove the fines and to obtain the desired 315-500 microns fraction. The catalyst had a molybdenum content of 6% wt.

Example 17

The catalyst of this Example was prepared by the physical mixing method. The zeolite powder was calcined at a temperature of 500° C. for 4 hours to convert it to $H^+$ form. Then, 0.8739 g $MoO_3$ was mixed in a grinder with 10 g of the zeolite powder. The mixture was then placed in a microwave furnace and kept under nitrogen (1 L/min) at a temperature of 25° C. for 4 hours. Then, the temperature was ramped at 25° C./min to 500° C. and held for 2 hours. Next, the catalyst was cooled, mixed with 3% wt graphite and shaped into pellets with a 40 mm diameter and 5 mm height. The pellets were crushed, sieved to remove fines and obtain the desired 315-500 microns fraction for testing. The catalyst had a molybdenum content of 5.504% wt.

Example 18

An ammoniumheptamolybdate solution was prepared by dissolving 4.63 g of ammoniumheptamolybdate in 20 mL of deionized water. The volume of the solutions was then adjusted to 25 mL with deionized water to provide an impregnating solution with a molybdenum concentration of 0.15 mol/L. The zeolite powder was shaped by compacting it at 250 bar. The obtained zeolite support was calcined at a temperature of 500° C. for 4 hours. Then, an impregnation solution comprising 6.34 mL of the above ammoniumheptamolybdate solution and 2.66 g of deionized water was prepared and used to impregnate 10 g of the zeolite support in a porcelain dish. The freshly impregnated support was manually mixed with a spatula and then aged for 0.5 hrs. Then, the impregnate was placed in a programmable oven and dried under dry air (1 L/min) by increasing the temperature from ambient to 70° C. at a rate of 1° C. per minute and by holding at temperature for 10 hours. Then, the temperature was increased using the same rate to 120° C. and held for another 10 hours. Finally, using the same rate, the temperature was increased to 500° C. and held for 5 hours. The finished catalyst was sieved to remove the fines and to obtain the desired 315-500 microns fraction. The catalyst had a molybdenum content of 6% wt.

Example 19

The catalyst of this Example was prepared by the physical mixture method. The zeolite powder was calcined at a temperature of 500° C. for 4 hours to convert it to $H^+$ form. Then, 0.6383 g $MoO_3$ was mixed with 10 g of the zeolite powder in a grinder. The obtained mixture was then placed in a microwave furnace and heated under nitrogen (1 L/min) at a temperature of 25° C. for 4 hours. Then, the temperature was increased at a rate of 25° C. per minute to 500° C. and held for 2 hours. The catalyst was cooled, mixed with 3% wt graphite and shaped into pellets with a 40 mm diameter and 5 mm height. The catalyst was then crushed, sieved to remove fines and to obtain the desired 315-500 microns fraction for testing. The catalyst had a molybdenum content of 4.081% wt (equivalent to 6% wt of $MoO_3$).

Example 20

An ammoniumheptamolybdate solution was prepared by dissolving 3.247 g of ammoniumheptamolybdate in 10 mL of deionized water. Then, 10.0 mL of the ammoniumheptamolybdate solution was used to impregnate 10 g of the zeolite powder. The impregnation was done in a porcelain dish. Following the addition of the solution, the mixture was mixed manually with the aid of a spatula and the mix was aged for 0.5 hrs. The impregnated zeolite was then placed in a programmable oven and dried and calcined under dry air (1 L/min) by increasing temperature from ambient to 120° C. using a heating rate of 1° C. per minute and holding at temperature for 10 hours. Then, using the same heating rate, the temperature was increased to 500° C. and held for 6 hours. The finished catalyst was sieved to remove fines and to obtain the desired 315-500 microns fraction. The catalyst had a molybdenum content of 15% wt.

What is claimed is:

1. A methane aromatization catalyst comprising an oxide of an active metal or a compound thereof, and an inorganic oxide support wherein the active metal is added to the support as a metal oxalate, and wherein the active metal comprises molybdenum.

2. A catalyst as claimed in claim 1 wherein a promoter compound is added to the support.

3. A catalyst as claimed in claim 1 wherein the inorganic oxide support is a zeolite or zeolite-containing support.

4. A catalyst as claimed in claim 1 wherein the molybdenum concentration in the catalyst is in the range of from 4 to 15 wt %.

5. A catalyst as claimed in claim 1 wherein the molybdenum concentration in the catalyst is in the range of from 6 to 10 wt %.

6. A catalyst as claimed in claim 1 wherein the active metal further comprises germanium.

7. A catalyst as claimed in claim 1 wherein the active metal further comprises ruthenium.

8. A catalyst as claimed in claim 1 wherein the active metal further comprises rhodium.

9. A catalyst as claimed in claim 1 wherein the active metal further comprises silver.

10. A catalyst as claimed in claim 1 wherein the active metal further comprises tungsten.

11. A catalyst as claimed in claim 1 wherein the active metal further comprises rhenium.

12. A catalyst as claimed in claim 1 wherein the active metal further comprises platinum.

13. A catalyst as claimed in claim 1 wherein the active metal further comprises lead.

\* \* \* \* \*